United States Patent [19]

Shoher et al.

[11] Patent Number: 5,336,091

[45] Date of Patent: * Aug. 9, 1994

[54] MOLDABLE DENTAL MATERIAL AND METHOD

[76] Inventors: Itzhak Shoher, 50 Shlomo-Hamelech St., Tel-Aviv, Israel, 64386; Aharon E. Whiteman, J.L Perez St., Petach-Tikvah, Israel, 49206

[*] Notice: The portion of the term of this patent subsequent to Aug. 10, 2010 has been disclaimed.

[21] Appl. No.: 977,637

[22] Filed: Nov. 17, 1992

Related U.S. Application Data

[63] Continuation-in-part of Ser. No. 825,379, Jan. 24, 1992, abandoned, which is a continuation-in-part of Ser. No. 801,028, Dec. 2, 1991, abandoned.

[51] Int. Cl.$^5$ .............................................. A61C 5/00
[52] U.S. Cl. ...................................... 433/215; 433/222.1; 433/228.1; 106/35; 164/92.1; 164/97; 419/2; 419/23
[58] Field of Search ............... 106/35; 433/215, 207, 433/208, 228.1, 222.1; 164/80, 92.1, 97; 419/2, 23, 27

[56] References Cited

U.S. PATENT DOCUMENTS

| | | | |
|---|---|---|---|
| 3,502,466 | 3/1970 | Vickery | 75/208 |
| 4,355,980 | 10/1982 | Dwight | 433/226 |
| 4,554,218 | 11/1985 | Gardner et al. | 428/567 |
| 4,602,953 | 7/1986 | Wiech, Jr. | 75/228 |
| 4,689,197 | 8/1987 | Groll et al. | 419/23 |
| 4,742,861 | 5/1988 | Shoher et al. | 164/80 |
| 4,814,008 | 3/1989 | Shoher et al. | 75/252 |
| 4,990,394 | 2/1991 | Shoher et al. | 428/212 |
| 4,997,699 | 3/1991 | Shoher et al. | 428/212 |
| 5,094,689 | 3/1992 | Stuemke et al. | 106/35 |
| 5,143,692 | 9/1992 | van der Zel | 419/8 |

FOREIGN PATENT DOCUMENTS

| | | |
|---|---|---|
| 0052922 | 2/1982 | European Pat. Off. . |
| 1271157 | 4/1972 | United Kingdom ........... B22F 5/00 |

*Primary Examiner*—Paul Lieberman
*Assistant Examiner*—Margaret Einsmann
*Attorney, Agent, or Firm*—E. Lieberstein

[57] ABSTRACT

A moldable dental composition for use in forming or repairing dental restorations composed of a mixture of high- and low-fusing temperature metal particles and a volatile binder, composed substantially or entirely of wax, with the binder having a concentration of between thirty (30%) to eighty percent (80%) by volume of the mixture. The average particle size of the high-fusing metal particles are above one micron, and preferably between four microns and eighty microns in size. The composition is heat treated at a temperature to melt the low-fusing temperature metal particles and to eliminate the binder, leaving a porous metal structure with a void volume above thirty percent (30%). The voids are filled using a filler material of metal or ceramic.

17 Claims, 1 Drawing Sheet

MOLDABLE DENTAL MATERIAL AND METHOD

FIELD OF THE INVENTION

This invention is a continuation-in-part of U.S. Ser. No. 07/825,379, filed Jan. 24, 1992 now abandoned, in the name of Shoher, et al., which, in turn, in a continuation-in-part of U.S. Ser. No. 801,028, filed Dec. 2, 1991 now abandoned, and relates to a moldable dental material composition and to a method for forming and/or repairing ceramic-to-metal dental restorations using such material.

BACKGROUND OF THE INVENTION

A metal coping is used in dentistry in the construction of a dental crown and bridge. The metal coping functions as the understructure of the crown and is usually covered, for reasons of aesthetics, with a fired-on coating of ceramic porcelain composition or an acrylic. The metal coping supports the coating and provides the required structural strength and rigidity for the restored tooth to resist the forces of mastication.

The customary practice is to cast the metal coping from an investment of a wax or plastic pattern of the tooth to be restored. The restoration formed using this procedure is conventionally referred to as a cast metal restoration. A metal coping has recently been developed for constructing a porcelain to metal crown which does not require waxing, investing or casting. The coping is formed from a prefabricated metal foil arranged in a prefolded configuration, with a plurality of foldable sections, as described in more detail, in U.S. Pat. No. Re. 33,099, which issued to applicant on Oct. 24, 1989. An alternative method of forming a dental coping from a metal foil is taught by applicant in U.S. Pat. No. 4,861,267, which issued on Aug. 29, 1989. In each instance, the starting material for forming the coping is a solid metal foil formed from a lamination of solid metal layers, each of a precious metal. The preferred arrangement is a lamination of layers of palladium disposed between gold or gold alloy layers, as taught by applicant in another U.S. Pat. No. 4,698,021 issued on Oct. 6, 1987. To form a coping from a preformed metal foil, the foil must be fitted and adapted to the die of the tooth to be restored and then swedged to conform to the die. The adaptation procedure is intended to be practiced by a dental technician in the dental laboratory and requires training and skill to achieve accuracy in getting a good fit at the margin.

SUMMARY OF THE INVENTION

A dental composition has been discovered which can be molded with minimal skill for forming a metal coping directly on a refractory die, or for repairing a dental restoration. This can be readily practiced either at the dental laboratory or by the dentist in the dental office.

In applicant's U.S. Pat. Nos. 4,742,861 and 4,990,394, a dental material composed of high- and low-fusing temperature metal particles is disclosed for forming, repairing, or reinforcing a dental restoration. The composition of metal particles are loose particles, preferably held together with a liquid binder such as glycerol, to form a paste or putty constituency which facilitates using the composition as a build-up material for reinforcing the framework of a dental restoration. The material is intended to be applied to a die, shaped into a desired configuration, and heat-treated. A porous sponge-like structure is formed as a result of the heat treatment, having the shape it was given prior to heat treatment. A low-melting temperature filler material may be melted into the sponge-like structure to form an integral solid mass.

Heretofore it was very difficult to consistently reproduce porous metal structures with identical properties and even more difficult to accurately control the void volume of the porous structure after heat treatment. The preparation of the composition was as critical as the relationship of the particles to the void volume of the porous structure. Too many variables affected consistency of the composition and it was difficult to maintain a homogeneous mixture of particles. As such, there was no assurance that each structure would have identical properties and the latitude to make adjustments in the composition was limited, without affecting shrinkage of the porous metal structure during heat treatment. It has now been discovered that by using a volatile binder, composed substantially or entirely of wax, with the binder having a minimum concentration of at least about thirty percent (30%) by volume of the total dental composition, the void volume of each porous structure will be essentially identical to one another and will closely conform to the concentration of the binder in the dental composition before heat treatment. The high content of the binder results in a porous structure after heat treatment, with a highly uniform capillary network of voids, which assures repeatability and is a significant factor in minimizing shrinkage. The properties of the porous structure are also more easily controlled by adjustment of the metal composition, volume ratio, etc.

The composition of the present invention broadly comprises: a uniform mixture of high-fusing temperature metal particles having an average particle size between 4 to 80 microns, and a melting temperature above a preselected heat treatment temperature; low-fusing temperature metal particles having a melting temperature equal to or below said preselected heat treatment temperature; and a volatile binder, composed substantially or entirely of wax, with the binder having a concentration of between about thirty percent (30%) and eighty percent (80%) by volume of the total composition, such that upon heat treatment at said heat treatment temperature, a porous metal structure is formed having a capillary network of voids and a void volume of between thirty (30%) to eighty percent (80%).

The method of the present invention for forming or repairing a dental restoration comprises the steps of:

forming a mixture composed of particles of high-fusing temperature metal, particles of low-fusing temperature metal, and a binder, into a desired shape, with the binder composed substantially or entirely of wax in a concentration of at least about thirty percent (30%) by volume of the total mixture;

heat treating the mixture at a temperature below the melting temperature of the high-fusing temperature metal particles, and at or above the melting temperature of the low-fusing temperature metal particles, to form a porous structure corresponding to said conformed shape and composed of said metals with a void volume of between thirty (30%) to eighty percent (80%);

adding a filler material to said porous structure; and heat treating the structure at a temperature below the melting temperature of the high-fusing metal, but high enough to melt said filler material into said porous structure for solidifying said structure into a solid.

BRIEF DESCRIPTION OF THE DRAWINGS

Additional advantages of the present invention will become apparent from the following detailed description of the invention when read in conjunction with the accompanying drawings of which.

DETAIL DESCRIPTION OF A PREFERRED EMBODIMENT OF THE INVENTION

Figure 1:
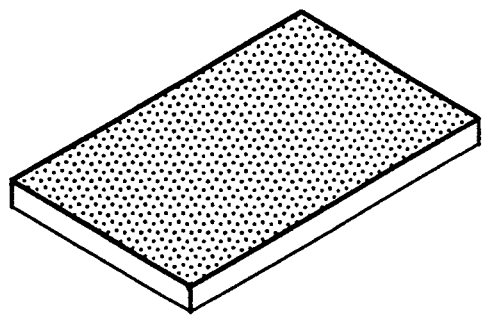
FIG. 1 is a perspective view of a compacted strip formed from the dental composition of the present invention.

The dental material of the present invention is a moldable composition formed from a mixture of metal particles of high- and low-fusing temperature metals and a volatile binder, composed substantially or entirely of wax. The concentration of the binder must be at least about thirty percent (30%) by volume of the mixture, and up to eighty percent (80%). Upon heat treatment, the binder vaporizes, leaving a porous, sponge-like structure having multiple voids uniformly distributed throughout the structure, with a void volume of at least thirty percent (30%). The high content of wax and other volatile constituents in the binder leaves an accurate network of capillary passages between the voids upon heat treatment. The uniformity and homogeneity in the network of voids has been found to be essential for making a dental restoration in accordance with the present invention. The voids formed in the heat-treated material on a volume basis ("void volume") may range between thirty (30%) to eighty percent (80%) by volume, and preferably between forty (40%) and sixty-five percent (65%) by volume. The high concentration of binder in the dental composition, of itself, unexpectedly provides substantial control over the void configuration and void volume of the porous metal sponge, with the void volume after heat treatment being directly related to the concentration of the binder before heat treatment.

In accordance with the present invention, a filler material is melted into the voids of the heat-treated porous structure to solidify the structure for forming the final dental restoration. The porous metal structure may be shaped into a desired configuration for forming a dental restoration before the filler material is added. The filler material may be any suitable ceramic or metal composition, preferably a precious metal composition. It is a preferred embodiment of the present invention to form a matrix of particles of filler material, which is mixed with a wax binder having a composition and concentration similar to the composition and concentration of the binder used to form the porous structure from the mixture of and high- and low-fusing temperature metal particles. A minimum binder concentration of at least about thirty percent (30%) by volume is preferred, and up to eighty-five percent (85%) by volume. At least fifty percent (50%) of the overall weight of the filler composition is preferably of individual or alloyed particles, of any size, containing between 90% to 98.5% gold and between 1.5% to 8.5% silver, preferably 2% to 5%, with the remainder selected from the group of metals such as copper, zinc, aluminum, magnesium, gallium, indium, tin, or any of the platinum group metals and/or elements from the third or fourth groups of elements of the periodic table. The weight of the remainder should not exceed seven percent (7%) of the total weight. The other fifty percent (50%) of the filler composition may be composed entirely of gold, although other metals may be included, provided the silver content of the total filter composition is limited to no more than ten percent (10%) by weight, and the total of the other metals is also limited to ten percent (10%) by weight. The addition of metals, other than gold and silver, may be added to provide a melting gradient during melting of the filler material.

The binder is composed substantially or entirely of wax, with a minimum wax content of at least fifty percent (50%). The composition of the wax itself is not critical to the invention, and any natural wax, mineral wax, organic wax or synthetic resinous wax composition may be used. The preferred wax is relatively soft and tacky, and should melt relatively cleanly, as should all of the other binder constituents, without leaving a significant residue. The vaporizing temperature of the binder must be below the melting temperature of the low-fusing temperature metal particles, and below the melting temperature for the filler material. Moreover, the high- and low-fusing temperature metal particles should combine with the binder to form a mixture with a uniform distribution of metal particles in the binder. Alternatively, the binder can be heated and the particles added and mixed, to form a uniform distribution of metal particles. The binder may include additives to control the malleability of the composition, and as a substitute for wax. The additives may be selected from elastomers, gums, synthetic rubbers, polysaccharides, and any organic or hydrocarbon compound similar to wax, such as paraffin oil. The additives should have a desirable vaporizing temperature at or below the heat treatment temperature, and should not leave a residue upon heat treatment.

The high-fusing temperature metal component of the base mixture of high- and low-fusing temperature metal particles may be of a single metal or metal alloy, preferably of precious metals such as platinum and/or palladium, in any desired proportion relative to each other, with or without other constituents such as gold, silver, copper, magnesium, aluminum, zinc, gallium, indium, and other metals or elements from the third, fourth, or fifth group of elements of the periodic table. Gold may be added to the high-fusing temperature metal component to increase the affinity of the high-fusing temperature metal component to the low-fusing temperature metal component. However, to minimize shrinkage at the dental margin, it is preferable but not critical to the present invention that a predetermined proportion of the high-fusing metal component contain a relatively high concentration of platinum and palladium in accordance with the following criteria: that at least fifty percent (50%) of the high-fusing particles, by weight, contains an alloy of at least about twelve percent (12%) of each element, platinum and palladium, and at least twenty percent (20%) gold. This requirement for platinum and palladium is not satisfied by a less concentrated amount distributed throughout the total overall high-fusing composition, nor does it require multiplying the required concentration for the predetermined proportion to compute the total high-fusing composition, i.e., the remainder of the composition can be devoid of platinum and palladium, with the understanding that the high-fusing component must retain its high-fusing temperature characteristic. The effect of a high concentration of platinum and palladium in at least a predetermined proportion on shrinkage at the dental margin is not completely understood. However, if the concentration of the high-fusing component is below the minimum amounts specified above, contraction at the dental margin may occur upon heat treatment.

The particles of low-fusing temperature metal are composed preferably of gold or a gold alloy, with gold as the major constituent. The preference for gold as the major constituent of the low-fusing component is based on its known characteristics of workability, biocompatibility, nonoxidizing properties, and color. The particles of high- and low-fusing temperature metal should be selected with the high-fusing temperature component having an average size above one (1) micron and preferably between four (4) microns and eighty (80) microns. The average size of the low-fusing temperature metal particles should preferably be no greater than 40 microns. The volume relationship of the metals in the mixture should be in a range of from about twenty (20%) to eighty percent (80%) of the low-fusing component relative to the high-fusing component, and preferably from forth (40%) to sixty-five percent (65%). The composition of the selected metal particles for the high- and low-fusing components will determine the optimum volume ratio. The weight ratio will vary with the specific gravity of the selected materials, as evidenced by the examples at the end of the specification. The high-fusing particle may have any shape, although an irregular flake-like shape is preferred.

The concentration of the volatile binder in the base mixture of high- and low-fusing temperature metal particles predominantly controls the void volume of the porous structure after heat treatment, as well as the uniformity of the capillary network formed between the voids which, in turn, controls the absorption and accommodation of the filler material in the porous structure. The heat treatment must eliminate the binder, preferably without leaving a residue, and cause the low-fusing particles to melt to form a stable porous metal structure with a thirty (30%) to eighty percent (80%) void volume and a uniformly distributed void matrix. The void volume will substantially correspond in percent to the percent concentration of binder before heat treatment, provided it is above the minimum concentration of thirty percent (30%).

In accordance with the preferred method of the invention, the base mixture of binder and high- and low-fusing temperature metal particles are compressed into a compacted strip (10), as shown in FIG. 1 in the form of a rectangular sheet, although any geometrical shape may be formed, including a cylindrical rod-like shape. The sheet may have any thickness of up to several millimeters, depending upon the specific application, with a thickness between 100 to 500 microns preferred, for forming a dental coping. The filler material and wax may, likewise, be compacted into a strip or other geometry, for ease of application to the porous structure formed from the base mixture.

Figure 1A:
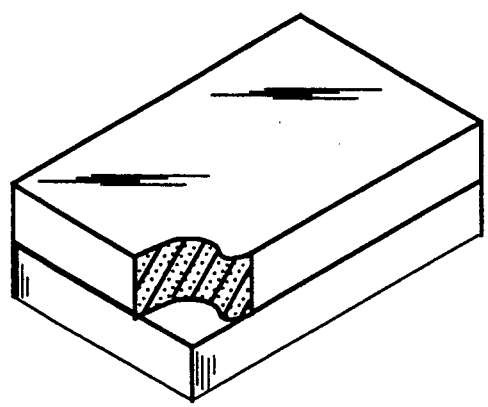
FIG. 1A is a view similar to FIG. 1 of a compacted strip formed of two layers.

Different metal-wax mixtures may be used to form laminated layers for special applications where, for example, it is preferable to have a variation in the void volume characteristic of the porous structure formed after heat treatment. For example, a compacted strip (10) composed of two layers, as shown in FIG. 1A, may be formed with one layer having twice as much binder as the other. This will result in a porous structure which has roughly twice the void volume in its exterior or interior, depending on whether the interior or exterior has the higher binder concentration. Moreover, the layer thickness may be varied and/or different metal alloy compositions may be used to form each layer. The number of layers in the strip (10), their composition, arrangement, and thickness can be used to predetermine the properties of the porous structure.

The filler material-wax composition may also be formed into a compacted strip (not shown) or may be laminated over the strip (10) of base material, similar to FIG. 1A. If they are preclad, it is still essential that the heat treatment be at a first temperature which will form a porous structure without melting the filler material. However, the wax component in each layer may be volatilized or be otherwise eliminated through melting. Thereafter, the heat treatment temperature may be raised to melt the filler material into the voids of the porous structure. Although the filler material should not melt or disturb the sintering process of the base material, components of the filler material, such as fluxes, binders, etc., may indeed melt into the porous structure during this first heat treatment.

When the porous sponge-like structure is formed from an independent strip (10) of base material, the filler material may have a sintering temperature of more or less than that of the sintering temperature of the low-fusing temperature metal particles in the base material. The second heat treatment causes the filler metal to melt into the porous sponge to fill the voids. It should be noted that the first heat treatment forms metal joints connecting the high-fusing temperature particles together. The joints are formed of an alloy of high- and low-fusing metals, and has a melting temperature above the melting temperature of the low-fusing metal. Accordingly, the second heat treatment temperature can be higher than the first heat treatment temperature without melting the joints.

To form a coping from a strip (10) of base material, the strip (10) is preferably cut into pieces or sections which are applied to the surface of a die. The pieces are hand-molded, using pressure, with or without the use of an adhesive. The adhesive may be composed of a wax with a solvent and may include other components, such as other adhesive agents, fluxes, etc. Hand-molding is done with the aid of a spatula or other hand instrument. The carving of the base metal-wax material into a preferred shape may be done on a model and then removed, or supported in any other fashion, for heat treatment. The heat treatment may be done in a furnace or under or over a flame. The usual heat treatment temperature range for the base material is between 800° C. and 1200° C. The heat treatment of the filler material may also be done in a furnace or using a flame.

Figure 2:
FIG. 2 is a transparency in perspective of the waxed coping hand-molded over the die of a prepared tooth, with the coping shown opened to illustrate thickness.
Figure 3:
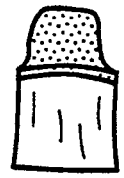
FIG. 3 is a perspective of the metal coping formed on the die of FIG. 2 after heat treatment.
Figure 4:
FIG. 4 is an illustration in perspective of the finished dental coping of FIG. 3 upon removal from the die.

The pieces of wax-strip (10) are easily shaped or carved into any desired geometry, as shown in FIG. 2, with little effort and require no expertise. The wax coping can be several millimeters in thickness. The heat treatment may be carried out directly on the die, with the wax absorbed into the die, leaving a sponge-like structure, as shown in FIG. 3. As the temperature is raised to the sintering temperature, the binder burns out and the sinterization process forms the spongy structure. Filler material is then added to the porous structure and heat treated to form a dense solid coping, as shown in FIG. 4. Once the metal coping is formed in accordance with the present invention, any conventional porcelain or acrylic veneer may be applied thereover to form a conventional ceramic-to-metal restoration.

The following are examples illustrating the volume-weight relationship between the low- and high-fusing temperature metals in the base metal composition for three different high-fusing metal compositions. In all of the following examples, the particle sizes, surface textures, etc., are identical from example to example.

EXAMPLE 1

The relationship between low-fusing and high-fusing metals in the metal composition that reflects differences in their specific gravity.

| Alloy (specific gravity gr/cm³)* | | Volume % | | Weight % | |
|---|---|---|---|---|---|
| Low Fusing | High Fusing | Low Fusing | High Fusing | Low Fusing | High Fusing |
| (A) | | | | | |
| Au (19.3)* | Pt (21.43)* | 30 | 70 | 27.8 | 72.2 |
| melting temperature | | | | | |
| 1063° C. | 1773° C. | | | | |
| (B) | | | | | |
| Au (19.3)* | Au 87% Pt 7% Pd 8% (17.8)* | 30 | 70 | 31.7 | 68.3 |
| melting temperature | | | | | |
| 1063° C. | 1187° C. | | | | |
| (C) | | | | | |
| Au (19.3)* | Pd (12.0)* | 30 | 70 | 40.8 | 59.2 |
| melting temperature | | | | | |
| 1063° C. | 1554° C. | | | | |

EXAMPLE 2

Examples of weight relations in composition of 50% wax binder and 50% metals (=low-fusing+high-fusing) by volume.

| Specific Gravity (gr/cm³) | | Volume % | | Weight % | |
|---|---|---|---|---|---|
| Metal Composition | Wax | Metals | Wax | Metals | Wax |
| (A) | | | | | |
| (20.8) | (0.9) | 50 | 50 | 95.85 | 4.15 |
| (B) | | | | | |
| (18.0) | (0.9) | 50 | 50 | 95.24 | 4.76 |
| (C) | | | | | |
| (14.2) | (0.9) | 50 | 50 | 94.04 | 5.96 |

EXAMPLE 3

Volume and weight relations of different mixtures of a metal composition of (A) and a wax binder.

| Volume % | | Weight % | |
|---|---|---|---|
| Metal | Wax | Metal | Wax |
| 25 | 75 | 88.50 | 11.50 |
| 50 | 50 | 95.85 | 4.15 |
| 75 | 25 | 98.58 | 1.42 |

Metal specific gravity is 20.8 g/cm³.
Wax specific gravity is 0.9 g/cm³.

These examples prove that the palladium will increase the stability of the material during the sinterization of the sponge, so that it retains the same dimensions without shrinking in conformity to the material before sinterization. The platinum component enhances the flow of the filler into the sponge.

It should be understood that the dental material of the present invention can be used for repair work or to join two restorations at the interproximal. The repair work can be of a preformed metal restoration or of a cast metal restoration.

What is claimed:

1. A moldable dental composition comprising: a uniform mixture of high-fusing temperature metal particles having an average particle size between about 4 to 80 microns, and a melting temperature above a heat treatment temperature; low-fusing temperature metal particles having a melting temperature equal to or below said heat treatment temperature; and a volatile binder, composed substantially or entirely of wax, with the binder in a concentration of between about thirty percent and eighty percent by volume, such that upon heat treatment at said heat treatment temperature, a porous metal structure is formed having a capillary network of voids and a void volume of between thirty to eighty percent.

2. A moldable dental composition, as defined in claim 1, wherein said high- and low-fusing temperature metal particles are precious metals.

3. A moldable dental composition, as defined in claim 2, wherein the low-fusing temperature metal component, relative to the high-fusing temperature component, is between twenty to eighty percent by volume.

4. A moldable dental composition, as defined in claim 2, wherein the low-fusing temperature metal component, relative to the high-fusing temperature component, is between forty to sixty-five percent by volume.

5. A moldable dental composition, as defined in claim 3, wherein said high-fusing temperature metal particles contain a concentration of platinum and palladium in a major proportion by weight, with at least fifty percent of the high-fusing particles, by weight, containing an alloy comprising at least twelve percent of platinum and palladium, respectively, and at least twenty percent gold.

6. A moldable dental composition, as defined in claim 3, wherein the void volume of said porous structure is between thirty-five to sixty-five percent.

7. A moldable dental composition, as defined in claim 6, further comprising a filler material for solidifying the porous metal structure formed upon heat treatment of said uniform mixture of high- and low-fusing metal particles, comprising a composition having a melting temperature below the melting temperature of said high-fusing metal component.

8. A moldable dental composition, as defined in claim 7, wherein said filler material comprises gold and a wax binder with the wax binder in a concentration of at least about thirty percent by volume of said filler material.

9. A moldable dental composition, as defined in claim 8, wherein said filler material further comprises an alloy of at least fifty percent by weight of gold and a metal selected from the group consisting of silver, copper, zinc, aluminum, magnesium, gallium, indium, tin, any of the platinum group metals, and elements from the third and fourth groups of elements of the periodic table of elements. fourth groups of elements of the periodic table of elements.

10. A moldable dental composition, as defined in claim 9, wherein at least fifty percent of the filler composition by weight comprises from between 90% to 98.5% gold and between 1.5% to 8.5% silver.

11. A moldable dental composition, as defined in claim 9, further comprising a flux.

12. A method for forming or repairing a dental restoration, comprising the steps of:

forming a mixture composed of particles of high-fusing temperature metal, particles of low-fusing temperature metal, and a binder, into a desired shape, with the binder composed substantially or entirely of wax in a concentration of at least about thirty percent by volume of the total mixture;

heat treating the mixture at a temperature below the melting temperature of the high-fusing temperature metal particles, and at or above the melting temperature of the low-fusing temperature metal particles, to form a porous structure corresponding to said conformed shape and composed of said metals with a void volume of between thirty to eighty percent;

adding a filler material to said porous structure; and heat treating the structure at a temperature below the melting temperature of the high-fusing metal, but high enough to melt said filler material into said porous structure for solidifying said structure into a solid.

13. A method, as defined in claim 12, wherein said filler material comprises particles of gold and wax.

14. A method, as defined in claim 13, wherein said mixture is applied to a die or model of the tooth to be restored, and shaped into a coping of the desired shape for forming said structure.

15. A method, as defined in claim 14, wherein porcelain is applied to said solidified structure.

16. A method, as defined in claim 14, wherein said mixture is first formed into a strip, which is applied to said die or model of the tooth to be restored, and shaped into a desired configuration.

17. A method, as defined in claim 16, wherein said filler is in the form of a strip.

* * * * *